United States Patent [19]
Widin et al.
[11] Patent Number: 4,953,112
[45] Date of Patent: Aug. 28, 1990

[54] METHOD AND APPARATUS FOR DETERMINING ACOUSTIC PARAMETERS OF AN AUDITORY PROSTHESIS USING SOFTWARE MODEL

[75] Inventors: Gregory P. Widin, West Lakeland, Minn.; Mats B. Dotevall, Goteborg, Sweden

[73] Assignee: Minnesota Mining and Manufacturing Company, St. Paul, Minn.

[21] Appl. No.: 192,214

[22] Filed: May 10, 1988

[51] Int. Cl.[5] ........................ A61N 1/36; H04R 25/00
[52] U.S. Cl. ........................ 364/578; 73/585; 128/746
[58] Field of Search .............. 364/553, 571.02, 571.07, 364/578, 579, 413.02, 413.05; 371/20; 73/585; 128/746; 381/68; 379/1, 52

[56] References Cited

U.S. PATENT DOCUMENTS

| | | | |
|---|---|---|---|
| 4,289,143 | 9/1981 | Canavesio et al. | 73/585 |
| 4,425,481 | 10/1984 | Mangold et al. | 381/68.2 |
| 4,548,082 | 10/1985 | Engebretsen et al. | 73/585 |
| 4,577,641 | 3/1986 | Hochmair et al. | 73/585 |
| 4,586,194 | 4/1986 | Kohashi et al. | 73/585 |
| 4,622,440 | 11/1986 | Slavin | 381/68 |
| 4,675,835 | 6/1987 | Pfleiderer | 364/571.02 |
| 4,694,401 | 9/1987 | Higuchi | 364/553 |
| 4,713,782 | 12/1987 | Blackham | 364/553 |
| 4,748,598 | 5/1988 | Kopke | 73/585 |

OTHER PUBLICATIONS

Skinner, Margaret W., Hearing Aid Evaluation, Prentice Hall, Englewood Cliffs, N.J. (1988).
Briskey, Robert J. "Instrument Fitting Techniques".
Sandlin, Robert E., Hearing Instrument Science and Fitting Practices, National Institute for Hearing Instruments Studies, Livonia, Mich., pp. 439–494 (1985).
Green, David S., "Pure Tone Air Conduction Testing", Chapter 9.
Katz, Jack, Editor, Handbook of Clinical Audiology, Williams & Wilkins, Baltimore, Md. (1978).
Adby, P. R. and Dempster, M. A. H., Introduction to Optimization Method, Chapman and Hall, London (1974).

*Primary Examiner*—Parshotam S. Lall
*Assistant Examiner*—Christopher L. Makay
*Attorney, Agent, or Firm*—Donald M. Sell; Walter N. Kirn; William D. Bauer

[57] ABSTRACT

A software model of the auditory characteristics of an auditory prosthesis is stored independently of the actual auditory prosthesis being fitted to determine the acoustic parameters to be utilized. A transfer function of the auditory characterictics of the individual auditory prosthesis to be fitted, or of an exemplary model of such an auditory prosthesis, is created, transformed into a table, or other usable form, and stored in software usable by the automated fitting program. The automated fitting program may then "test" or try by iterative process, the various settings for the acoustic parameters of the auditory prosthesis and determine accurately the results without actual resort the physical auditory prosthesis itself.

8 Claims, 5 Drawing Sheets

METHOD AND APPARATUS FOR DETERMINING ACOUSTIC PARAMETERS OF AN AUDITORY PROSTHESIS USING SOFTWARE MODEL

BACKGROUND OF THE INVENTION

The present invention relates generally to auditory prostheses and more particularly to auditory prostheses having adjustable acoustic parameters.

Auditory prostheses have been utilized to modify the auditory characteristics of sound received by a user or wearer of that auditory prosthesis. Usually the intent of the prosthesis is, at least partially, to compensate for a hearing impairment of the user or wearer. Hearing aids which provide an acoustic signal in the audible range to a wearer have been well known and are an example of an auditory prosthesis. More recently, cochlear implants which stimulate the auditory nerve with an electrical stimulus signal have been used to compensate for the hearing impairment of a wearer. Other examples of auditory prostheses are implanted hearing aids which stimulate the auditory response of the wearer by a mechanical stimulation of the middle ear and prostheses which otherwise electromechanically stimulate the user.

Hearing impairments are quite variable from one individual to another individual. An auditory prosthesis which properly compensates for the hearing impairment of one individual may not be beneficial or may be disruptive to another individual. Thus, auditory prostheses must be adjustable to serve the needs of an individual user or patient.

The process by which an individual auditory prosthesis is adjusted to be of optimum benefit to the user or patient is typically called "fitting". Stated another way, the auditory prosthesis must be "fit" to the individual user of that auditory prosthesis in order to provide a maximum benefit to that user, or patient. The "fitting" of the auditory prosthesis provides the auditory prosthesis with the appropriate auditory characteristics to be of benefit to the user.

This fitting process involves measuring the auditory characteristics of the individual's hearing, calculating the nature of the acoustic characteristics, e.g., acoustic amplification in specified frequency bands, needed to compensate for the particular auditory deficiency measured, adjusting the auditory characteristics of the auditory prosthesis to enable the prosthesis to deliver the appropriate acoustic characteristic, e.g., acoustic amplification is specified frequency bands, and verifying that this particular auditory characteristic does compensate for the hearing deficiency found by operating the auditory prosthesis in conjunction with the individual. In practice with conventional hearing aids, the adjustment of the auditory characteristics is accomplished by selection of components during the manufacturing process, so called "custom" hearing aids, or by adjusting potentiometers available to the fitter, typically an audiologist, hearing aid dispenser, otologist, otolaryngologist or other doctor or medical specialist.

Some hearing aids are programmable in addition to being adjustable. Programmable hearing aids have some memory device which store the acoustic parameters which the hearing aid can utilize to provide a particular auditory characteristic. The memory device may be changed or modified to provide a new or modified auditory parameter or set of auditory parameters which in turn will provide the hearing aid with a modified auditory characteristic. Typically the memory device will be an electronic memory, such as a register or randomly addressable memory, but may also be other types of memory devices such as programmed cards, switch settings or other alterable mechanism having retention capability. An example of a programmable hearing aid which utilizes electronic memory is described in U.S. Pat. No. 4,425,481, Mangold et al. With a programmable hearing aid which utilizes electronic memory, a new auditory characteristic, or a new set of acoustic parameters, may be provided to the hearing aid by a host computer or other programming device which includes a mechanism for communicating with the hearing aid being programmed.

In order to achieve an acceptable fitting for an individual, changes or modifications in the acoustic parameters may need to be made, either initially to achieve an initial setting or value for the acoustic parameters or to revise such settings or valuations after the hearing aid has been used by the user. Known mechanisms for providing settings or valuations for the acoustic parameters usually involve measuring the hearing impairment of an individual and determining the setting or value necessary for an individual acoustic parameter in order to compensate for the hearing impairment so measured.

A persistent problem in such fitting procedures is that the measuring and the adjustments in the acoustic parameters during fitting must be made using the auditory prosthesis itself which provides some practical difficulties. If the fitting procedure is automated, as is sometimes the case, the automatic features of the fitting process must be stopped and a physical, usually mechanical, adjustment of the acoustic parameters must be made while the auditory prosthesis is operated or utilized in conjunction with the user. Such manual, physical processes not only consume a lot of time but also involve the user, patient, of the auditory prosthesis and, thus, makes the fitting process long and arduous for the patient.

SUMMARY OF THE INVENTION

The present invention provides a method and an apparatus for determining the acoustic parameters for an auditory prosthesis without the manual, arduous, time consuming steps required in the past.

The present invention utilizes a software model of the auditory prosthesis which may be stored independently of the actual auditory prosthesis being fitted to determine the acoustic parameters to be utilized. A transfer function of the auditory characteristics of the individual auditory prosthesis to be fitted, or of an exemplary model of such an auditory prosthesis, is created, transformed into a table, or other usable form, and stored in software usable by an automated fitting program. The automated fitting program may then "test" or try by iterative process, the various settings for the acoustic parameters of the auditory prosthesis and accurately determine the results without actual resort to the physical auditory prosthesis itself. Since the transfer function of the auditory prosthesis is stored in software, it is no longer necessary to halt the automated fitting process to physically adjust the auditory prosthesis. The automated fitting process, thus, remains automated and the fitting process is greatly accelerated and enhanced. Further, since less time is required for each step in the fitting process, a greater accuracy may be obtained in the same amount of fitting time. Alternatively, since less time is required for each step, the fitting process may be accelerated and more patients may be treated by the technician in the same amount of time.

The present invention is designed for use with an auditory prosthesis having acoustic parameters which at least in part determine at least one of the acoustic fitting functions of the auditory prosthesis, the acoustic parameters being adjustable, and provides a method of determining the acoustic parameters of the auditory prosthesis which will provide a user of the auditory prosthesis with a target auditory response by following the steps of determining the target auditory response of the user, determining the acoustic fitting function of the auditory prosthesis operating in conjunction with the user, and optimizing the acoustic parameters of auditory prosthesis by comparing the auditory response of the acoustic fitting function with the target auditory response and by adjusting the acoustic parameters to minimize the error of the comparison.

The present invention is also designed for use with an auditory prosthesis having acoustic parameters which at least in part determine the acoustic fitting function of the auditory prosthesis, the acoustic parameters being adjustable, and provides a method of determining the acoustic parameters of the auditory prosthesis which will provide a user of the auditory prosthesis with a target auditory response, by following the steps of determining the target auditory response of the user, determining the acoustic fitting function of the auditory prosthesis operating in conjunction with the user, storing a software model of the acoustic fitting function, and optimizing the acoustic parameters of auditory prosthesis by comparing the auditory response of the software model with the target auditory response and by adjusting the acoustic parameters to minimize the error of the comparison.

The present invention is also designed for use with an auditory prosthesis having acoustic parameters which at least in part determine the acoustic fitting function of the auditory prosthesis, the acoustic parameters being adjustable, and provides an apparatus for determining the acoustic parameters of the auditory prosthesis which will provide a user of the auditory prosthesis with a target auditory response. A first mechanism determines the target auditory response of the user. A second mechanism is adapted to be operably coupled to the user and determines the acoustic fitting function of the auditory prosthesis operating in conjunction with the user. An optimization mechanism is operably coupled to the first mechanism and the second mechanism and optimizes the acoustic parameters of auditory prosthesis by comparing the auditory response of the acoustic fitting function with the target auditory response and adjusting the acoustic parameters to minimize the error of the comparison.

The present invention is also designed for use with an auditory prosthesis having acoustic parameters which at least in part determine the acoustic fitting function of the auditory prosthesis, the acoustic parameters being adjustable, and provides an apparatus for determining the acoustic parameters of the auditory prosthesis which will provide a user of the auditory prosthesis with a target auditory response. A first mechanism determines the target auditory response of the user. A second mechanism is adapted to be operably coupled to the user and determines the acoustic fitting function of the auditory prosthesis operating in conjunction with the user. A storage mechanism is operably coupled to the second mechanism and stores a software model of the acoustic fitting function. An optimization mechanism is operably coupled to the first mechanism and the second mechanism and optimizes the acoustic parameters of auditory prosthesis by comparing the auditory response of the software model with the target auditory response and for adjusting the acoustic parameters to minimize the error of the comparison.

BRIEF DESCRIPTION OF THE DRAWINGS

The foregoing advantages, construction and operation of the present invention will become more readily apparent from the following description and accompanying drawings in which.

DETAILED DESCRIPTION OF THE PREFERRED EMBODIMENTS

Figure 1:
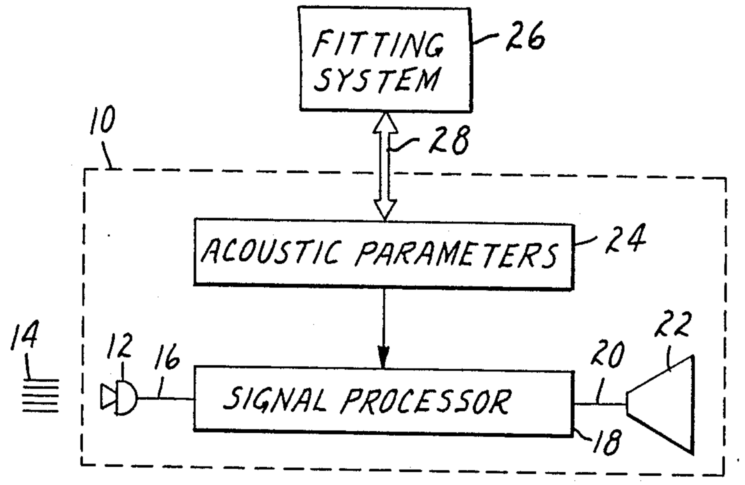
FIG. 1 PRIOR ART
FIG. 1 is a block diagram of a prior art fitting system operating in conjunction with an auditory prosthesis.

FIG. 1 illustrates a prior art auditory prosthesis 10, which in this description is described as being a hearing aid. The auditory prosthesis has a microphone 12 for receiving an acoustic signal 14 and converting the acoustic signal 14 into an electrical signal 16 for transmission to a signal processor 18. The signal processor 18 operates on the electrical input signal 16 and provides a processed electrical signal 20 which is transmitted to a receiver 22 to be transformed into a signal which is perceptible to the user of the auditory prosthesis 10. The auditory prosthesis 10 illustrated in FIG. 1 is adjustable in its auditory characteristics. The auditory characteristic of the auditory prosthesis 10 is determined by a set of acoustic parameters 24 stored within the auditory prosthesis 10, preferably, or in any other convenient retrievable location. The signal processor 18 modifies the electrical input signal 16 in accordance with a set of acoustic parameters 24 to provide the processed electrical signal 20. The set of acoustic parameters 24 define the auditory characteristic of the auditory prosthesis 10. An example of such an auditory prosthesis includes a signal processor such as is described in U.S. Pat. No. 4,425,481, Mangold et al which is hereby incorporated by reference. Receiver 22, which in hearing aid parlance is a miniature speaker, which produce a signal which is adapted to be perceptible to the user of the auditory prosthesis 10 as sound. Since the set of acoustic parameters 24 is modifiable, or in one embodiment may be selected from a plurality of sets of acoustic parameters 24, the auditory characteristic of a particular auditory prosthesis 10 is adjustable and is determined, at least in part, by the set of acoustic parameters 24.

In order to provide the user of the auditory prosthesis 10 with an appropriate auditory characteristic, as specified by the set of acoustic parameters 24, the auditory prosthesis 10 must be "fit" to the individual's hearing impairment. The fitting process involves measuring the auditory characteristic of the individual's hearing, calculating the nature of the amplification or other signal processing characteristics needed to compensate for a particular hearing impairment, determining the individual acoustic parameters 24 which are to be utilized by the auditory prosthesis 10 and verifying that these acoustic parameters do operate in conjunction with the individual's hearing to obtain the compensation desired With the programmable auditory prosthesis 10 as illustrated in FIG. 1, the adjustment of the set of acoustic parameters 24 occurs by electronic control from a fitting apparatus 26 which communicates with the auditory prosthesis 10 via communication link 28. Usually, fitting apparatus 26 is a host computer which may be programmed to provide an initial "fitting", i.e., to determine the initial values for the set of acoustic parameters 24 in order to compensate for a particular hearing impairment for a particular individual with which the auditory prosthesis 10 is intended to be utilized. Such an initial "fitting" process is well known in the art. Examples of techniques which can be utilized for such a fitting process may be obtained by following the technique described in Skinner, Margaret W., *Hearing Aid Evaluation,* Prentice Hall, Englewood Cliffs, N.J. (1988), the entire content of which is hereby incorporated by reference, especially Chapters 6–9. Similar techniques can be found in Briskey, Robert J., "Instrument Fitting Techniques", in Sandlin, Robert E., *Hearing Instrument Science and Fitting Practices,* National Institute for Hearing Instruments Studies, Livonia, Mich. (1985), pp. 439–494, which are hereby incorporated by reference.

Figure 2:
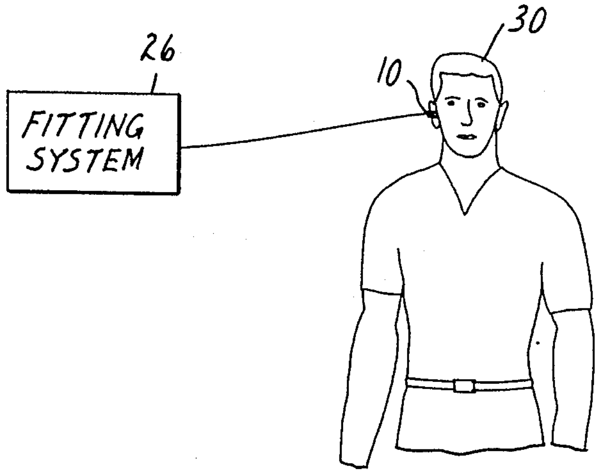
FIG. 2 PRIOR ART
FIG. 2 is a schematic illustration of a prior art fitting system operating during the fitting process.

FIG. 2 illustrates such a prior art fitting system 26 being operated in conjunction with a programmable auditory prosthesis 10 which is being fit to an individual or patient 30. In operation, the fitting system 26 is used in conjunction with the auditory prosthesis 10 coupled to the individual 30 in order to determine and adjust the auditory prosthesis 10 to properly compensate for the individual's 30 hearing impairment.

Figure 3:
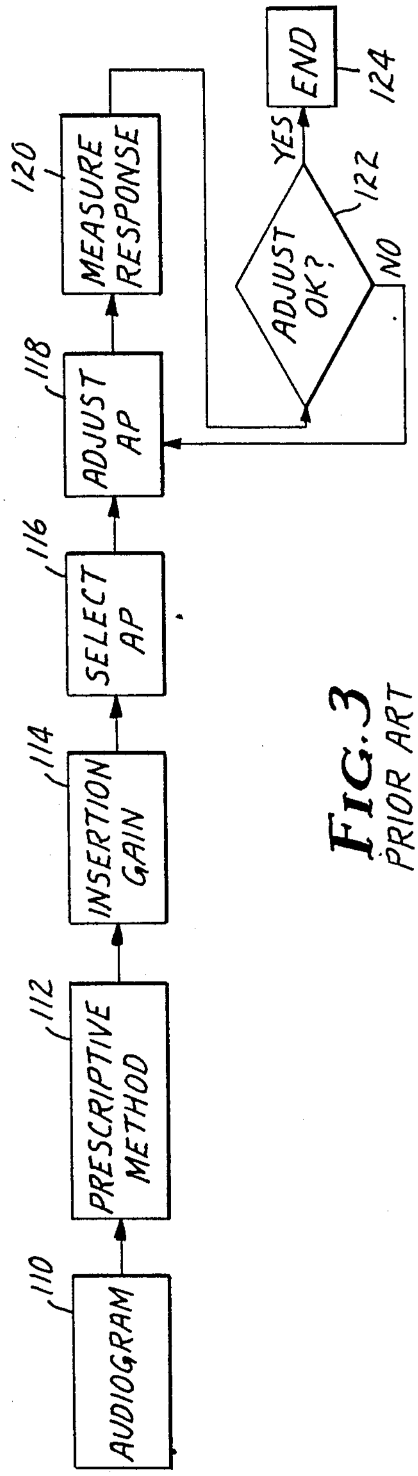
FIG. 3 PRIOR ART
FIG. 3 is a flow chart illustrating the prior art fitting system.

This prior art process is illustrated in FIG. 3. First, an audiogram 110 is made of the individual's 30 hearing impairment by standard well known techniques. Such as is described Green, David S., "Pure Tone Air Conduction Testing", Chapter 9, in Katz, Jack, editor, *Handbook of Clinical Audiology,* Williams & Wilkins, Baltimore, Md. (1978). The audiogram 110 represents the actual auditory ability of the individual 30 and, hence, illustrates or represents the hearing impairment of the individual 30. From the hearing impairment of the individual 30, as represented by the audiogram 110, the prescriptive method, or compensation of the hearing impairment, 112 can be developed, also by well known techniques. From the prescriptive method 112 an insertion gain 114 is determined. That is, once the prescriptive method 112, or the compensation needed for this individual's 30 hearing impairment has been determined, the settings of the acoustic parameters 24 of the auditory prosthesis 10 can be determined at step 114. Once the insertion gain 114 is determined, a particular auditory prosthesis is selected 116 and adjusted 118 according to that insertion gain 114. With the auditory prosthesis 10 adjusted as in step 118, the actual response of the individual 30 is measured 120. From the the measured response 120, it can be determined whether the auditory prosthesis 10 is adjusted properly (step 122). If the auditory prosthesis, at this point, is adjusted properly, the process ends (step 124). If, however, the auditory prosthesis is not adjusted properly (step 122), the process must revert back to step 118 where the auditory prosthesis 10 is readjusted to a new or better approximation of an auditory characteristic and the response is again measured at block 120. Again, it is determined whether or not the auditory prosthesis is adjusted properly at step 122. Thus, an iterative adjustment and measurement of the response of the individual 30 occurs This well known adjustment/fitting technique is represented in the prior art fitting system as illustrated by block 26 in FIGS. 1 and 2. It can be seen that the entire process for fitting system 26, as illustrated in FIG. 3 must be done with the auditory prosthesis 10 operating in conjunction with the individual 30. Thus, depending upon the length of the iterative process, the individual 30 is subjected to a long and arduous fitting process with the auditory prosthesis being utilized in conjunction with the individual's 30 ear. Since much time is spent for each fitting step, a fewer number of iterative processes can be performed in the same amount of time, resulting in potentially high in accuracy in the fitting process.

Figure 4:
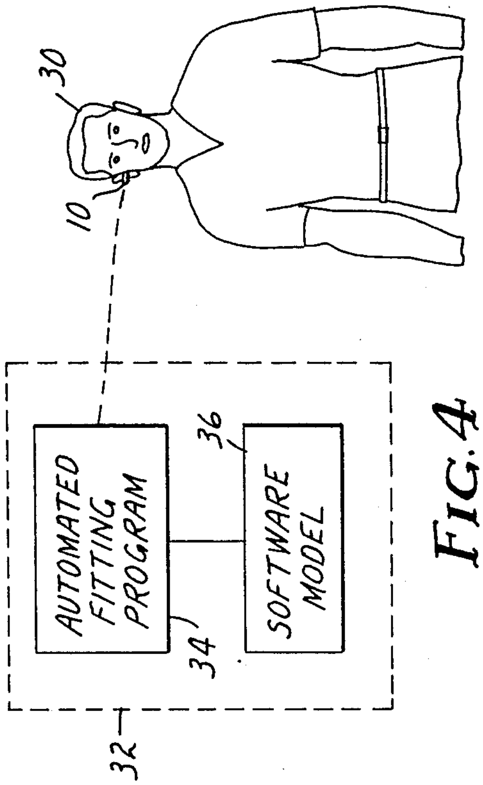
FIG. 4 is a schematic illustration of the fitting system of the present invention operating during the fitting process.

FIG. 4 illustrates a fitting system 32 of the present invention operating in conjunction with an auditory prosthesis 10, again being fitted to individual 30. Fitting system 32 contains an automated fitting program 34 which may operate either in conjunction with the auditory prosthesis 10 or with a software model 36 of the auditory prosthesis 10 which is stored in, or retrievable by, fitting system 32.

Figure 5:
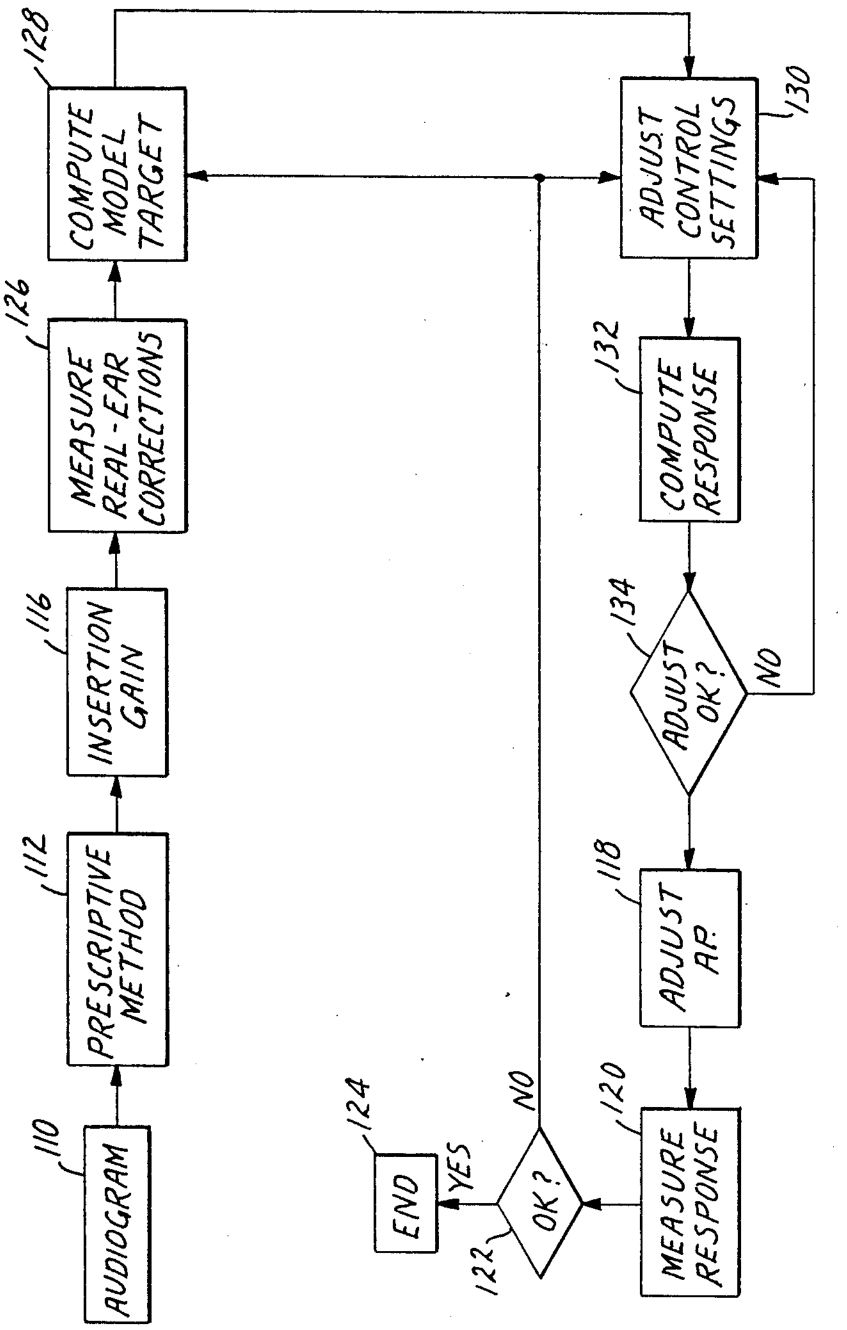
FIG. 5 is a flow diagram of the fitting system utilizing the present invention.

The procedures involved in the fitting system 32 are illustrated in FIG. 5. As in the prior art fitting systems 26, fitting system 32 starts with an audiogram 110 of the individual's 30 hearing. This technique is well known and exactly the same as it is performed in the prior art fitting system 26 illustrated in FIG. 3.

Again as in FIG. 3, the procedure in FIG. 5 develops a prescriptive method 112 from the audiogram 110. From the prescriptive method 112 an insertion gain that is the desired auditory characteristic of the auditory prosthesis 10 is determined. The determination of the prescriptive method 112 and the development of the insertion gain are exactly the same as they occur in the prior art fitting system 26 illustrated in FIG. 3. With fitting system 32, a real ear measurement 126 of the auditory prosthesis 10 operating in conjunction with the individual 30 is obtained by the automated fitting program 34. The technique used to perform the real ear measure 126 will be described later. From the real ear measure 126 and the insertion gain 116 determined previously, a target response of the auditory response is computed 128. The computed target response 128 simply takes the insertion gain as determined by 116 and it modifies that insertion gain according to the real ear measured 126 corrections. Thus, the computed target response 128 simply represents a combination of the insertion gain 116 and the real ear measure corrections 126. The fitting system 32 then "adjusts" 130 the acoustic parameters which would determine the auditory characteristics of the auditory prosthesis. This "adjustment" is performed utilizing a software model 36 of the auditory prosthesis contained in the fitting system 32. Thus, the adjustment 130 need not be performed with the fitting system 32 coupled to the auditory prosthesis 10. The adjustment 130 can be performed independently and separately from any connection to the auditory prosthesis 10 and, hence, the individual 30 is not encumbered at this point. From the software model 36, the presumed response 132 of the auditory prosthesis 10 is computed. Since the fitting system 32 contains a software model 36, it is not necessary to actually operate the auditory prosthesis 10 with the calculated acoustic parameters 24, but it is merely necessary to utilize the software model 36 to compute the projected response 132. Step 134 determines whether the presumably properly "adjusted" auditory prosthesis 10 has the proper values of acoustic parameters 24 to provide the auditory characteristic as determined by the computed target response 128. If the adjustment determination at step 134 indicates, based upon the software model 36, that the presumed auditory prosthesis 10 will not operate properly, then the process reverts to the "adjustment" 130 step and the acoustic parameters of the auditory prosthesis 10 are readjusted, based upon known techniques, to new values where a new computed response 132 may be obtained and a new determination as to the proper adjustment of the presumed auditory prosthesis 10 may be performed (step 134). If the adjustment, however, is proper, then the process optionally ends or (as shown) the auditory prosthesis is adjusted 118 with that set of acoustic parameters 24 and the actual response of the auditory prosthesis 10 is measured 120. If this adjustment of the auditory prosthesis 10 is proper (step 122), then the process is ended (step 124). If at step 122, after actually measuring the auditory prosthesis 10 in conjunction with the individual 30, it is determined that the adjustment is not proper, the process returns to recompute the target response at step 128 or to readjust the control settings at step 130 in order to revise and obtain a new computed response 132 and the process is again accomplished from that point forward.

It is to be noted that only step 110 (determining the audiogram) and steps 118–124 (actually measuring the output) need be performed in conjunction with the individual 30. The remainder of the iterative adjustment technique contained in steps 128–134 may be performed by the fitting system 32 with the automated fitting program 34 operating in direct conjunction with the software model 36 and without utilization, of or connection with, the actual auditory prosthesis 10 or any encumbrance of the individual 30. Thus, individual 30 avoids the long, arduous, iterative adjustment techniques involved in processing the fitting system 32.

The use of the software model 36 can be also illustrated with reference to the block diagram shown in FIG. 6. In this diagram, the individual's 30 target auditory characteristic is determined at block 210 (embodying blocks 110, 112 & 114 in FIG. 5). This target auditory response can be developed by known techniques. Further, the acoustic characteristics of the individual's 30 ear, i.e., a real ear measurement, is accomplished at block 212. This real ear measurement is similar to block 126 illustrated in FIG. 5. The electrical response of the actual auditory prosthesis 10 is determined in block 214. This can be accomplished by measuring the auditory characteristics of an auditory prosthesis 10, i.e., its acoustic input to output characteristics, with the auditory prosthesis 10 being operated separately from the individual 30.

Thus, block 210 determines the target auditory characteristic of the individual, e.g., by the performance of an audiogram and subsequent calculation, and the acoustic real ear measurement 212 of the auditory prosthesis 10 on individual 30 is determined. In addition, actual measurements are taken of the electro-acoustic response to 14 of the auditory prosthesis 10 but this need not be done in conjunction with the individual 30 nor at the same time. From the acoustic characteristics of the real ear measurement from block 212 and the electrical response of the auditory prosthesis 10, a software model 36 of the auditory prosthesis 10 may be constructed. Using known optimization techniques at block 216, the target auditory characteristics from block 212 can be compared with the characteristics of the software model of the auditory prosthesis 10 from block 36 to adjust the values of the software model's parameters so as to minimize any error between the target auditory response from block 212 and the response of the software model 36. Using these known optimization techniques, the best fit for the auditory prosthesis 10 can be obtained at block 218.

Figure 6:
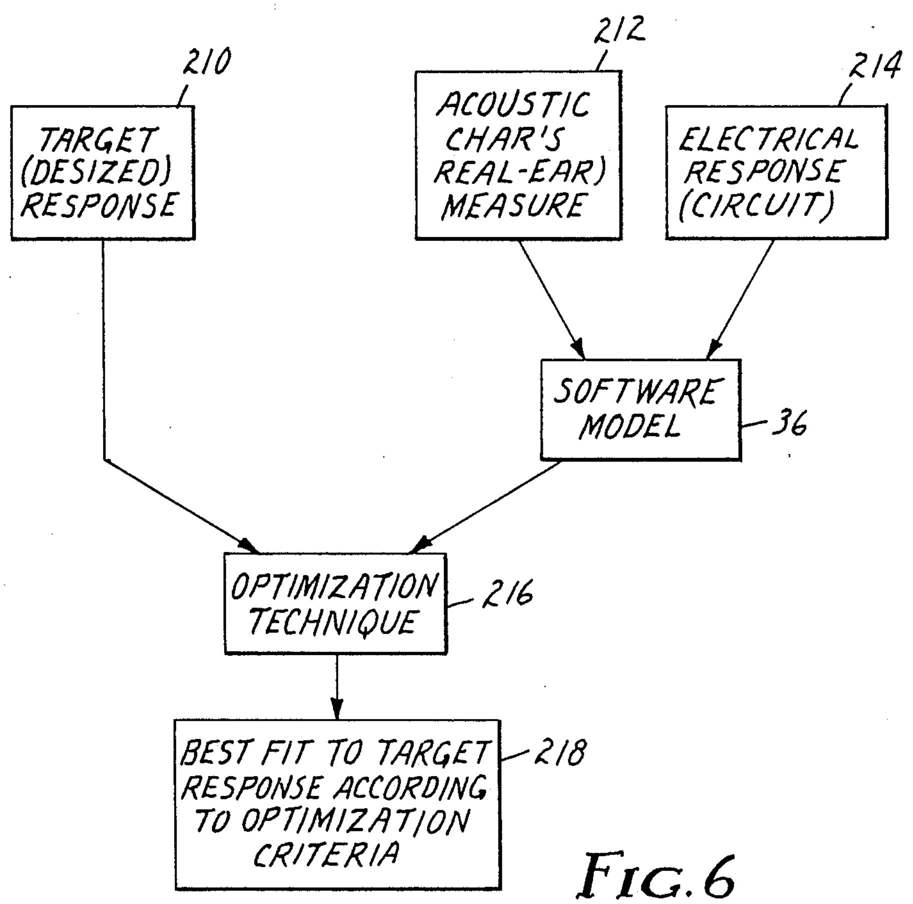
FIG. 6 is a block diagram illustration of a fitting system utilizing the present invention.
Figure 7:
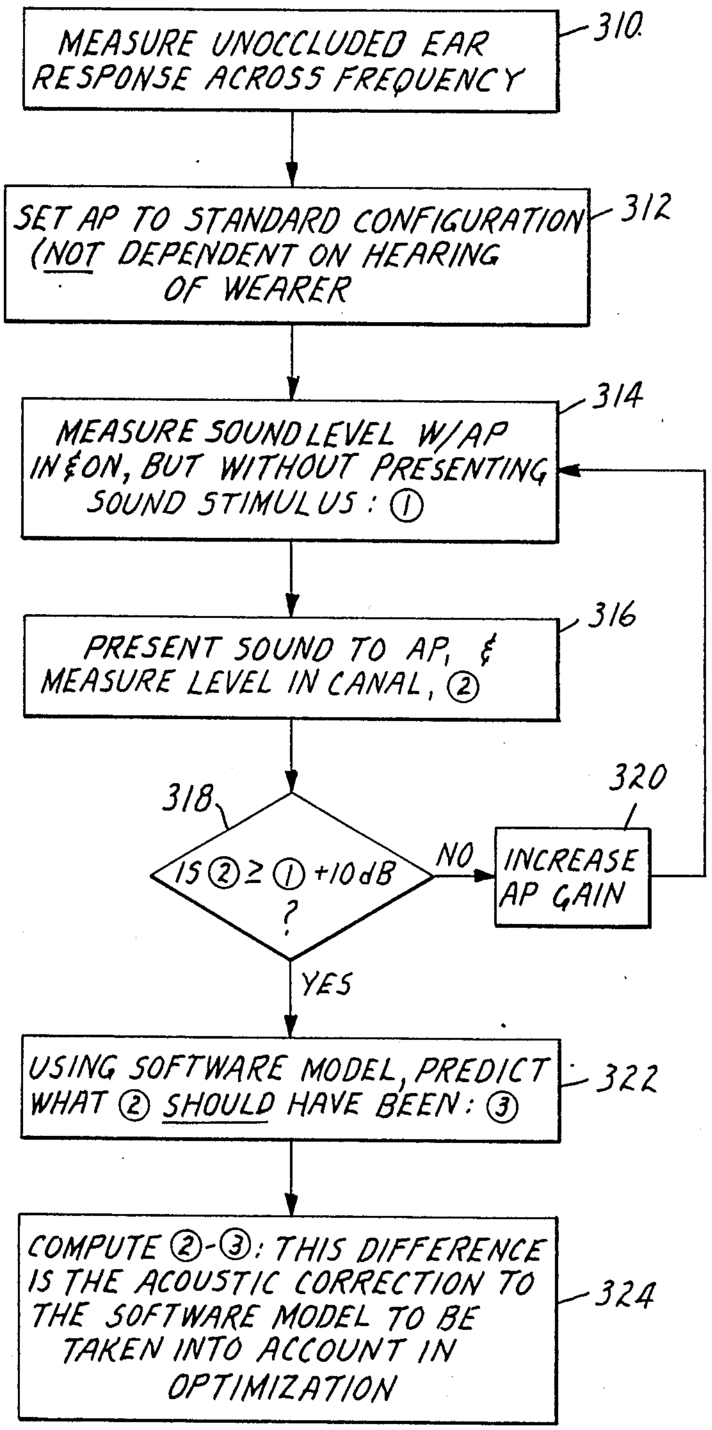
FIG. 7 is a block diagram illustration of the flow chart of the real ear measurement step of the fitting system utilizing the present invention.

The technique to obtain the real ear measurements as discussed in block 126 of FIG. 5 and block 212 of FIG. 6, may be had by reference to FIG. 7. The purpose of the real ear measurement is to obtain the acoustic characteristics of the auditory prosthesis 10 in combination with the individual's 30 external ear canal and any associated "plumbing", e.g., the ear mold, tubing, etc. These real ear measurements are commonly taken and utilized in conjunction with individuals. However, the usual technique is to insert a functioning auditory prosthesis 10 into the external ear canal or near the external ear canal of the individual 30 with the auditory prosthesis 10 "programmed" to provide the prescribed auditory characteristic to correct the individual's hearing impairment. The "real ear measurement" then obtains the actual response of the prescribed auditory characteristics correcting the hearing impairment of the individual. The real ear measurement technique illustrated in FIG. 7 utilizes the same real ear measurement technique except that first the unoccluded ear canal response is measured at block 310 across the entire frequency range with which the auditory prosthesis 10 is designed to be operated. Next, the auditory prosthesis 10, or in a less preferred embodiment a replica thereof dedicated to the fitting system 32, is set to a known standard configuration, which is not dependent upon the individual hearing impairment of the individual 30, and is operated in conjunction with the individual 30 and his external ear canal. This is illustrated by block 312. Without presenting a sound stimulus to the auditory prosthesis 10, the sound level is measured with a real ear measurement with the auditory prosthesis in the ear and operating as illustrated at block 314. An auditory stimulus is then presented to the auditory prosthesis 10, at block 316, and the real ear response is measured. At block 318, it is determined whether the measurement obtained in block 316 is at least 10 dB more than the measurement obtained in block 314. If not, the gain of the auditory prosthesis 10 is increased at block 320 and the process returns to step 314 where a new nonsound stimulus real ear measurement is obtained and then at block 316 where a sound stimulus response is measured and a new determination is made of whether the measurement at block 316 is at least 10 dB greater than the measurement made at block 314. This process is repeated until the auditory prosthesis 10 provides a response at block 316 which is at least 10 dB greater than the response measured in block 314 or until a present maximum allowable level is reached and operator intervention is required. The process, then at block 322, using the software model 36, predicts what the measurement at block 316 should have been based on the sound stimulus presented. Block 324 then computes the difference between the result from block 322 and the result obtained in block 316. The difference between these values becomes the real ear measurement correction discussed at block 126 in FIG. 5. Thus, the technique illustrated in FIG. 7 measures the appropriate "real ear" acoustics and the amount of compensation needed to supplement the software model 36 to apply to the particular individual 30.

The optimization technique illustrated in block 216 of FIG. 6, while being applied to the software model and the present invention, may be one of the many well known techniques for determining the proper values with a set of unknowns which can not be solved analytically. A preferred optimization technique involves a "constrained modified method of steepest descent" (sometimes referred to as a "gradient method"), using Newton accelerators. The constraints are the values of the set of acoustic parameters 24, e.g., a center frequency of between 500 and 4,000 Hertz and maximum power output which is not greater than the uncomfortable loudness level. The optimization criteria include centering, i.e., the center frequency being as close as possible to 1500 Hertz; the inband average error in both the high pass and low pass frequency bands and the absolute error of the entire amplitude over the entire frequency response of the auditory prosthesis 10, i.e., the dB difference between the model and the target auditory response. Successful optimization depends upon a good initial estimate of the values of the acoustic parameters which can be done with known auditory techniques. These initial estimate techniques are well understood in the art. As an example, the initial estimate for the crossover frequency is chosen as a weighted average of the frequencies $f_i$ at which the model response is calculated according to the formula:

$$f_{est} = e^{\left( \frac{\sum_i In(f_i) \cdot t_i}{\sum_i t_i} \right)}$$

Where In is the Naperian logarithm, $t_i$ is the target response at the $i^{th}$ frequency, and e=2.718281828. The summations are taken over the range of i which gives frequencies $f_i$ from the lowest to the highest at which the model is calculated (in this case 125–8000 Hz).

Minimizing the error resulting from specific values of acoustic parameters 24 involve trying a new value for the acoustic parameters and comparing the target insertion gain with the predicted response from the model. Through appropriate optimization techniques, this comparison can be made to find the minimum of the error function by moving in the proper direction "down" the error surface. Reference on how to obtain this optimization can be be found in Adby, P.R. and Dempster, M.A.H., *Introduction to Optimization Methods*, Chapman and Hall, London (1974).

Figure 8:
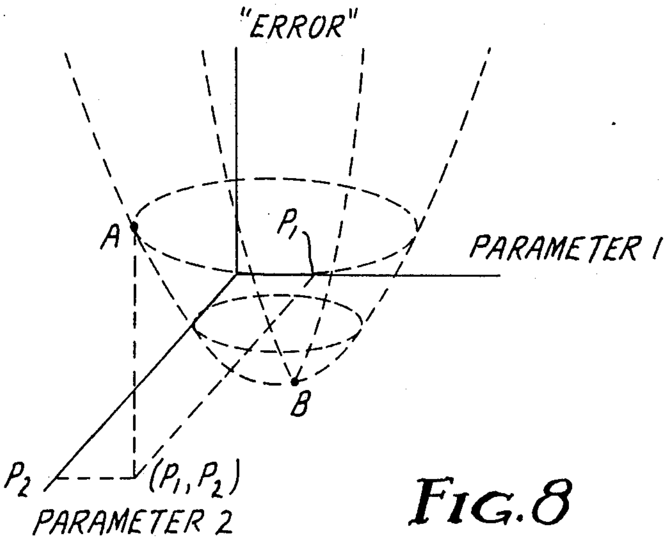
FIG. 8 illustrates an "error surface" encountered by an optimization technique.

FIG. 8 schematically illustrates the general optimization problem with more than one variable. The two parameters, 1 and 2 may be set to particular values arbitrarily. In this example, the error, computed as just described, describes a parabola as a function of parameters 1 and 2. In general, for a N-dimensional optimization, the error surface exists in a space of dimension (N +1). The goal is to find the minimum error. In the example given in FIG. 8, the initial choice of ($P_1$, $P_2$) results in a non-minimum error, as shown by point A on the error surface. The optimization algorithm must find the minimum point, point B, by search through the error space. Note that in general the error surface or function described analytically is not known. However, there are many methods developed to cope with this problem which involve, in general, evaluating equations.

In the software fitting system 32, the programmable parameters are: 1. Microphone attenuation, 2. Crossover frequency between low pass and high pass channels, 3. Attenuation in the low pass automatic gain control circuitry, 4. Attenuation in the low pass channel following the automatic gain control circuitry, 5. Attenuation in the high pass automatic gain control circuitry and 6. Attenuation in the high pass channel following the automatic gain control circuitry. There are two other programmable measures, low pass and high pass release time but they do not affect the frequency response and are not among the optimized quantities in the preferred embodiment. The following equations utilizing these programmable acoustic parameters 24 provide for the software model 36. The estimated IG(f) [in dB]= the acoustic correction (f) +microphone response (f) ++ internal amplifiers (f) + receiver response (f) + microphone attenuation (f) +20 ×$\log_{10}$ [$LP$ $(fc$-F)×$10^{(AGC}$L)/20 +HP (f-fc)×$10^{(AGC\text{-}H+ATT}$H/$^{20}$]+ constant. Where the notation X(f) is intended to indicate that the value of x is a function of frequency f. These equations describe the software model in the frequency domain. It is to be recognized and understood that other equations may also calculate the amplitude response of the auditory prosthesis when set to acoustic parameters 24.

Thus, it can be seen that there has been shown and described a novel method and an apparatus for determining the acoustic parameters of an auditory prosthesis. It is to be recognized and understood, however, that various changes, modifications and substitutions in the form and the details of the present invention may be made by those skilled in the art without departing from the scope of the invention as defined by the following claims.

What is claimed is:

1. For use with an auditory prosthesis having acoustic parameters which at least in part determine at least one of the acoustic fitting functions of said auditory prosthesis, said acoustic parameters being adjustable, a method of determining said acoustic parameters of said auditory prosthesis which will provide a user of said auditory prosthesis with a target auditory response, comprising the steps of:

determining said target auditory response of said user;

determining said acoustic fitting function of said auditory prosthesis operating in conjunction with said user; and optimizing said acoustic parameters of said auditory prosthesis by comparing the auditory response of said acoustic fitting function with said target auditory response and by adjusting said acoustic parameters to minimize the error of said comparison.

2. A method as in claim 1 wherein said determining said acoustic function step further comprises determining said acoustic fitting function based upon a software look-up table.

3. A method as in claim 1 wherein said determining said acoustic function step further comprises determining said acoustic fitting function based upon a set of mathematical equations to serve as said acoustic fitting function.

4. A method as in claim 3 wherein said optimizing step further comprises solving said set of mathematical equations for said acoustic parameters based upon said target auditory response.

5. For use with an auditory prosthesis having acoustic parameters which at least in part determine the acoustic fitting function of said auditory prosthesis, said acoustic parameters being adjustable, a method of determining said acoustic parameters of said auditory prosthesis which will provide a user of said auditory prosthesis with a target auditory response, comprising the steps of:

determining said target auditory response of said user;

determining said acoustic fitting function of said auditory prosthesis operating in conjunction with said user;

storing a software model of said acoustic fitting function;

optimizing said acoustic parameters of auditory prosthesis by comparing the auditory response of said software model with said target auditory response and by adjusting said acoustic parameters to minimize the error of said comparison.

6. A method as in claim 5 wherein said software model of said acoustic fitting function comprises a software look-up.

7. A method as in claim 5 wherein said software model of said acoustic fitting function comprises a set of mathematical equations to serve as said acoustic fitting function.

8. A method as in claim 7 wherein said optimizing step further comprises solving said set of mathematical equations for said acoustic parameters based upon said target auditory response.

* * * * *